United States Patent
Sweeney

(10) Patent No.: US 6,757,563 B2
(45) Date of Patent: Jun. 29, 2004

(54) CARDIAC RHYTHM MANAGEMENT SYSTEM WITH ULTRASOUND FOR AUTOCAPTURE OR OTHER APPLICATIONS

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/321,119

(22) Filed: Dec. 17, 2002

(65) Prior Publication Data

US 2003/0069608 A1 Apr. 10, 2003

Related U.S. Application Data

(63) Continuation of application No. 09/950,276, filed on Sep. 10, 2001, now Pat. No. 6,539,262, which is a continuation of application No. 09/294,641, filed on Apr. 19, 1999, now Pat. No. 6,298,269.

(51) Int. Cl.[7] ............................................. A61N 1/362
(52) U.S. Cl. ..................................................... 607/28
(58) Field of Search ............................... 607/9, 17, 19, 607/27–28, 4–6

(56) References Cited

U.S. PATENT DOCUMENTS

| | | | |
|---|---|---|---|
| 4,357,944 A | 11/1982 | Mauser et al. | 128/663 |
| 4,651,716 A | 3/1987 | Forester et al. | 128/1 D |
| 4,881,549 A | 11/1989 | Rhyne | 128/660.07 |
| 4,917,115 A | 4/1990 | Flammang et al. | 607/19 |
| 4,936,304 A | 6/1990 | Kresh et al. | 607/23 |
| 5,139,020 A | 8/1992 | Koestner et al. | 128/419 PG |
| 5,156,154 A | 10/1992 | Valenta, Jr. et al. | 128/661.09 |
| 5,156,157 A | 10/1992 | Valenta, Jr. et al. | 128/662 |
| 5,183,040 A | 2/1993 | Nappholz et al. | 128/419 PG |
| 5,188,106 A | 2/1993 | Nappholz et al. | 128/419 PG |

(List continued on next page.)

FOREIGN PATENT DOCUMENTS

| | | | |
|---|---|---|---|
| EP | 0503839 | 9/1992 | A61B/8/06 |
| EP | 0503285 | 10/1992 | A61B/8/06 |
| WO | WO-95/19806 | 7/1995 | A61N/1/365 |
| WO | WO-98/38911 | 9/1998 | A61B/5/042 |
| WO | WO-99/07285 | 2/1999 | A61B/8/00 |

OTHER PUBLICATIONS

"Realtime Position Management—Tracking Technology", *Cardiac Pathways Corporation*, www.cardiac.com/products_systems.html,(2001), 2 pgs.

(List continued on next page.)

*Primary Examiner*—Carl Layno
*Assistant Examiner*—B. Webb
(74) *Attorney, Agent, or Firm*—Schwegman, Lundberg, Woessner & Kluth, P.A.

(57) ABSTRACT

A cardiac rhythm management system provides ultrasound autocapture capability for determining whether a stimulation has evoked a desired response from the heart, and for adjusting an energy of the stimulation based on the observed response from the heart. A first ultrasound element is disposed on a lead in the heart. A second ultrasound element is disposed elsewhere in the heart or in the implanted device. An autocapture determination circuit determines whether motion of the heart chamber indicates a contraction in response to the stimulation, and adjusts the stimulation energy to provide only that energy which is needed to obtain capture. This saves energy, prolonging the life of the implanted device, minimizing the risk and expense to patient associated with early explantation and replacement of the implanted device. Other applications include using ultrasound for (1) determining the strength of heart contractions (2) determining dissociation between electrical and mechanical heart activity, (3) determining the volume of the heart, (4) determining the origin of sensed intrinsic electrical heart activity signals, (5) recognizing particular arrhythmias (6) disrupting cell membranes for lowering stimulation thresholds, (7) controlling the delivery of a steroid, and (8) obtaining blood flow information.

21 Claims, 8 Drawing Sheets

U.S. PATENT DOCUMENTS

| | | | |
|---|---|---|---|
| 5,197,467 A | 3/1993 | Steinhaus et al. | 128/419 PG |
| 5,220,924 A | 6/1993 | Frazin | 128/662.06 |
| 5,243,976 A | 9/1993 | Ferek-Petric et al. | 607/6 |
| 5,305,745 A | 4/1994 | Zacouto | 128/67 |
| 5,316,001 A | 5/1994 | Ferek-Petric et al. | 128/661.08 |
| 5,508,045 A | 4/1996 | Harrison et al. | 424/608 |
| 5,527,336 A | 6/1996 | Rosenbluth et al. | 606/192 |
| 5,544,656 A | 8/1996 | Pitsillides et al. | 128/661.04 |
| 5,546,949 A | 8/1996 | Frazin et al. | 128/662.06 |
| 5,609,612 A | 3/1997 | Plicchi et al. | 607/17 |
| 5,657,760 A | 8/1997 | Ying et al. | 128/660.03 |
| 5,676,162 A | 10/1997 | Larson, Jr. et al. | 128/899 |
| 5,676,651 A | 10/1997 | Larson, Jr. et al. | 604/33 |
| 5,693,091 A | 12/1997 | Larson, Jr. et al. | 612/3 |
| 5,702,430 A | 12/1997 | Larson, Jr. et al. | 607/1 |
| 5,722,419 A | 3/1998 | Semmlow et al. | 128/733 |
| 5,727,552 A | 3/1998 | Ryan | 128/653.1 |
| 5,738,096 A | 4/1998 | Ben-Haim | 128/653.1 |
| 5,749,831 A | 5/1998 | Baker | 600/301 |
| 5,752,971 A | 5/1998 | Rosenbluth et al. | 606/192 |
| 5,758,666 A | 6/1998 | Larson, Jr. et al. | 128/899 |
| 5,792,199 A | 8/1998 | Fayram et al. | 607/19 |
| 5,814,599 A | 9/1998 | Mitragotri et al. | 514/3 |
| 5,830,848 A | 11/1998 | Harrison et al. | 514/2 |
| 5,836,985 A | 11/1998 | Rostami et al. | 607/14 |
| 5,843,129 A | 12/1998 | Larson, Jr. et al. | 607/1 |
| 5,865,738 A | 2/1999 | Morcos et al. | 600/365 |
| 5,879,375 A | 3/1999 | Larson, Jr. et al. | 607/30 |
| 5,925,069 A | 7/1999 | Graves et al. | 607/36 |
| 5,948,771 A | 9/1999 | Danziger | 514/185 |
| 5,991,660 A | 11/1999 | Goyal | 607/14 |
| 6,024,703 A | 2/2000 | Zanelli et al. | 600/437 |
| 6,216,027 B1 | 4/2001 | Willis et al. | 600/424 |
| 6,277,077 B1 | 8/2001 | Brisken et al. | 600/459 |
| 6,398,736 B1 | 6/2002 | Seward | 600/466 |
| 6,421,565 B1 | 7/2002 | Hemmingsson | 607/17 |
| 6,443,894 B1 | 9/2002 | Sumanaweera et al. | 600/443 |
| 6,450,977 B1 | 9/2002 | Baxter-Jones | 600/591 |
| 6,491,639 B1 | 12/2002 | Turcott | 600/508 |

OTHER PUBLICATIONS

Ben–Haim, Shlomo A., "Catheter Navigation in Modern Electrophysiology", *Journal of Cardiovascular Electrophysiology, vol., No. 11,* (Nov. 2000), 1193–1195.

De Groot, Natasja M., et al., "Three–Dimensional Catheter Positioning During Radiofrequency Ablation in Patients: First Application of a Real–Time Position Management System", *Journal of Cardiovascular Electrophysiology, vol. 11, No. 11,,* (Nov. 2000), 1183–1192.

CARDIAC RHYTHM MANAGEMENT SYSTEM WITH ULTRASOUND FOR AUTOCAPTURE OR OTHER APPLICATIONS

CROSS-REFERENCE TO RELATED APPLICATION(S)

This application is a continuation of U.S. application Ser. No. 09/950,276, filed on Sep. 10, 2001, now issued as U.S. Pat. No. 6,539,262, which is a continuation of U.S. application Ser. No. 09/294,641, filed on Apr. 19, 1999, now issued as U.S. Pat. No. 6,298,269, the specifications of which are hereby incorporated by reference.

TECHNICAL FIELD

This invention relates generally to cardiac rhythm management systems and particularly, but not by way of limitation, to a cardiac rhythm management system with ultrasound autocapture capability for determining whether a stimulation has evoked a desired response from the heart.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is providing therapy at appropriate energy levels. In pacers, for example, pacing stimulations must have sufficient energy to capture the heart, that is, to initiate a resulting heart contraction. Delivering too much energy, however, will shorten the life of the battery powered implantable device. This, in turn, results in performing an earlier surgical explantation and replacement procedure, with its attendant risks and costs, both for the procedure and for the replacement device. Thus, there is a need to determine whether a cardiac rhythm management system is providing therapy at appropriate energy levels.

SUMMARY

This document describes, among other things, a cardiac rhythm management system with ultrasound autocapture capability for determining whether a stimulation has evoked a desired response from the heart, and for adjusting an energy of the stimulation based on the observed response from the heart. An autocapture determination circuit determines whether motion of the heart chamber indicates a contraction in response to the stimulation, and adjusts the stimulation energy to provide only that energy which is needed to ensure reliable capture. This saves energy, prolonging the life of the implanted device, minimizing the risk and expense to patient associated with early explantation and replacement of the implanted device.

In one embodiment, the cardiac rhythm management system includes a lead. The lead includes a distal end and a proximal end. The distal end of the lead is adapted for being disposed in or about a heart. The distal end of the lead includes a first ultrasonic element. An electronics unit is coupled to the proximal end of the lead. The electronics unit includes an ultrasound driving circuit and a signal processing circuit that includes an autocapture determination circuit. In a first further embodiment, a second ultrasonic element is adapted for being disposed in a heart chamber different from the first ultrasonic element. In a second further embodiment, a second ultrasonic element is in a case carrying the electronics unit.

This document also discloses using the ultrasound for applications other than the ultrasound capability, including but not limited to: (1) determining the strength of heart contractions, such as from the slope of a signal transduced from the ultrasound, (2) determining dissociation between electrical and mechanical heart activity, (3) determining the volume of the heart, such as at different times during the cardiac cycle, (4) determining the origin of sensed intrinsic electrical heart activity signals based at least in part on information obtained from the ultrasound, (5) recognizing particular arrhythmias based at least in part on information obtained from the ultrasound, (6) delivering ultrasound for disrupting cell membranes for lowering stimulation thresholds, (7) using ultrasound to control the delivery of a steroid, and (8) obtaining blood flow information based at least in part on information obtained from the ultrasound. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
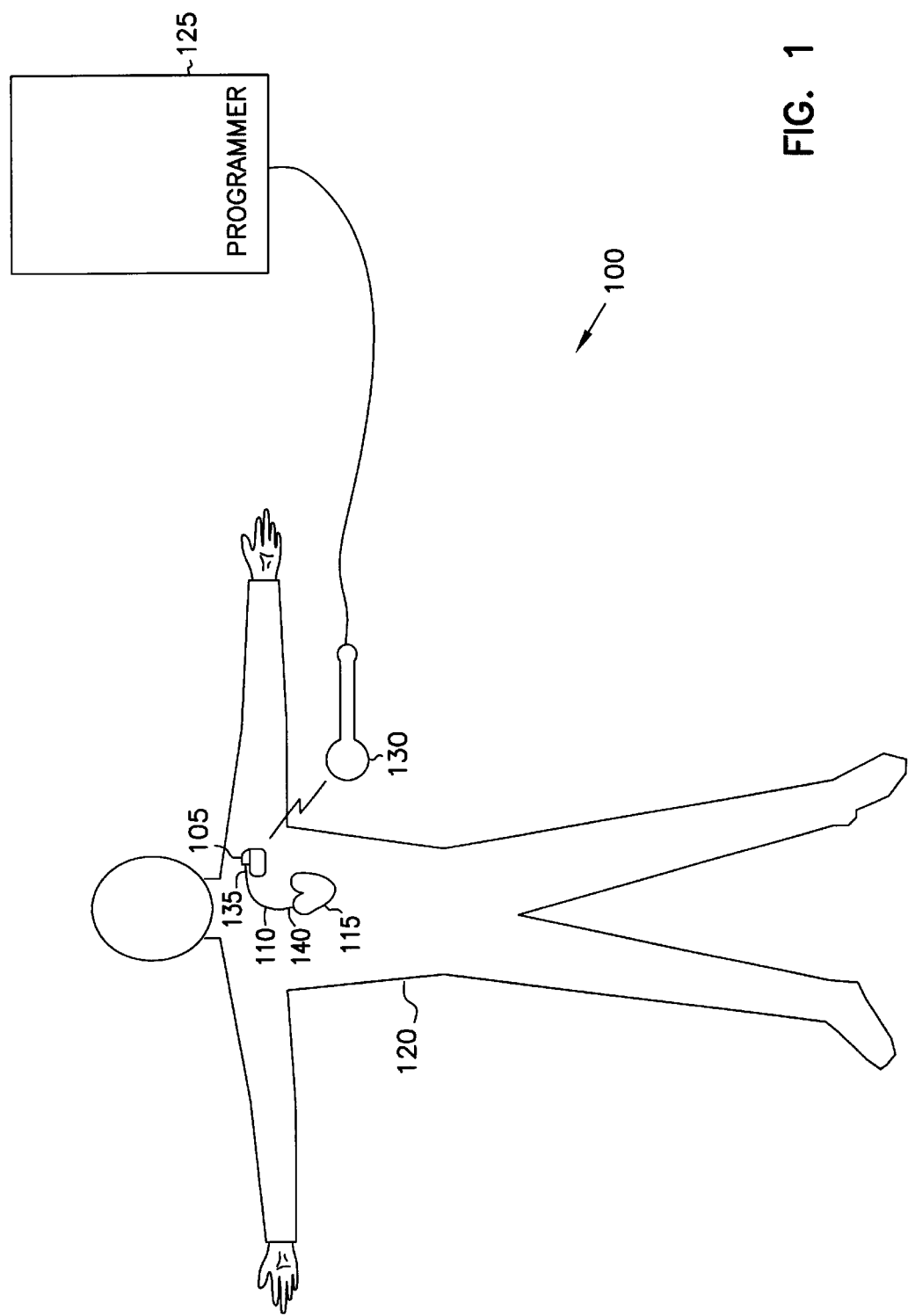
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

This document describes, among other things, a cardiac rhythm management system with ultrasound autocapture capability for determining whether a stimulation has evoked a desired response from the heart, and for adjusting an energy of the stimulation based on the observed response from the heart.

FIG. 1 is a schematic drawing illustrating generally, by way of example, but not by way of limitation, one embodiment of portions of a cardiac rhythm management system 100 and an environment in which it is used. In FIG. 1, system 100 includes an implantable cardiac rhythm management device 105, which is coupled by an intravascular endocardial lead 110 to a heart 115 of patient 120. System 100 also includes an external programmer 125 providing wireless communication with device 105 using a telemetry device 130. Lead 110 includes a proximal end 135, which is coupled to device 105, and a distal end 140, which is coupled to one or more portions of heart 115.

Figure 2:
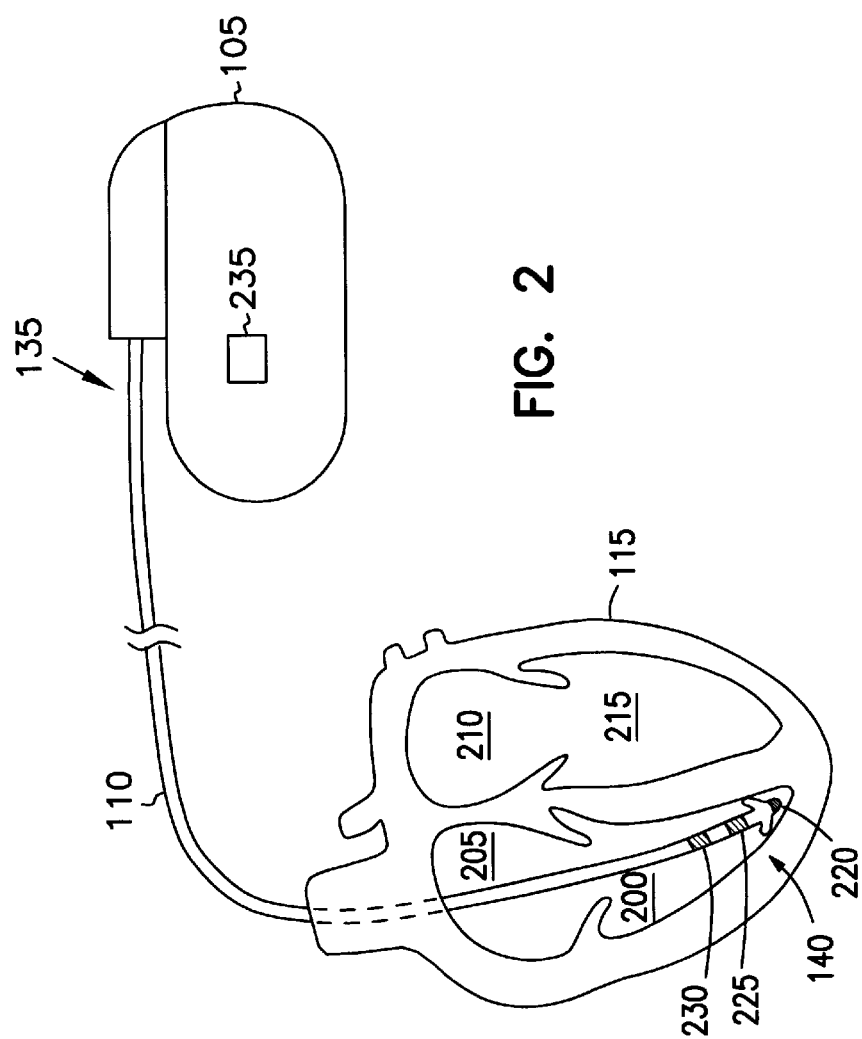
FIG. 2 is a schematic drawing illustrating generally one embodiment of portions of a lead and an implanted device.
Figure 6:
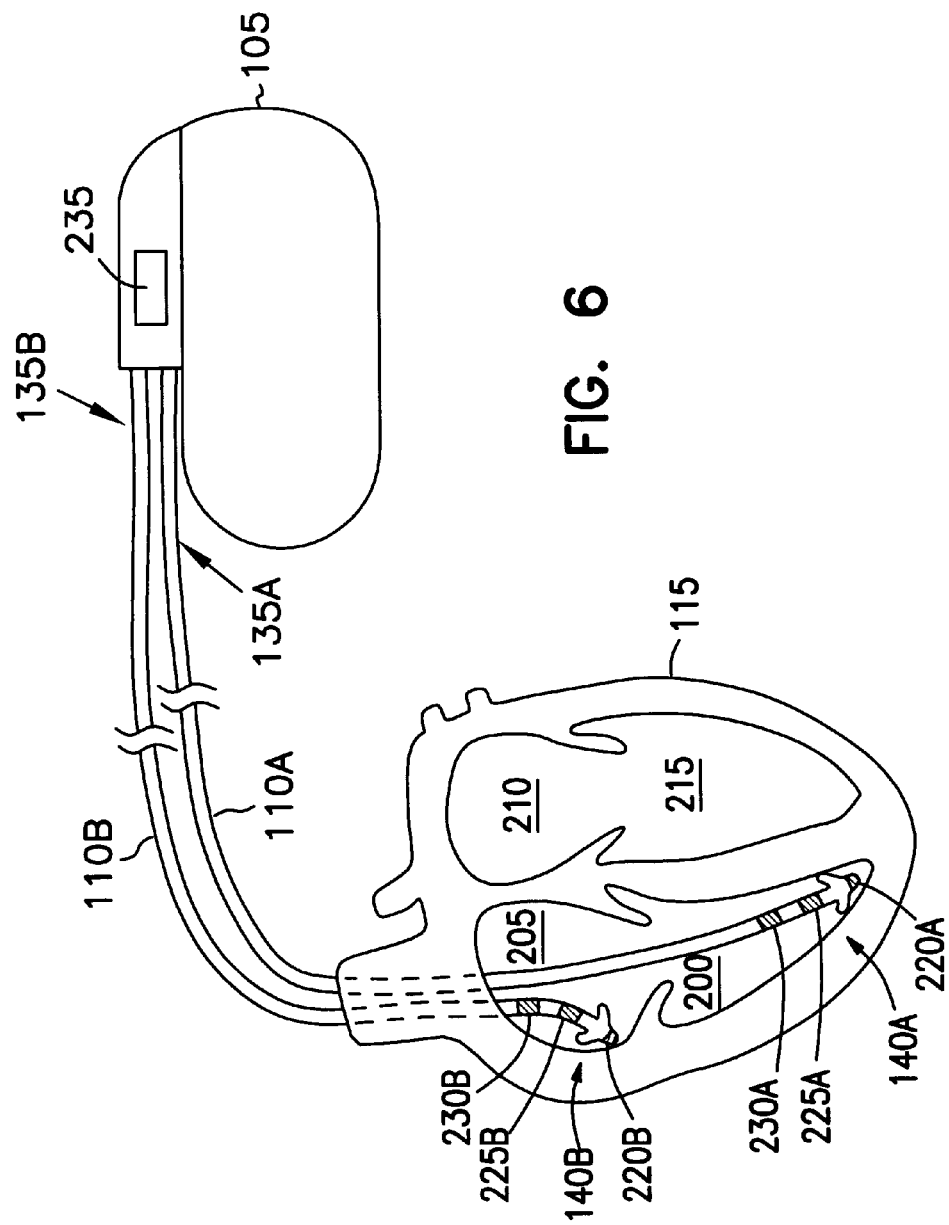
FIG. 6 is a schematic drawing illustrating generally an embodiment including a first ultrasonic element in a first heart chamber, a second ultrasonic element in another heart chamber, and a third ultrasonic element in the implanted device.

FIG. 2 is a schematic drawing illustrating generally, by way of example, but not by way of limitation, one embodiment of portions of lead 110 and device 105, with distal end 140 of lead 110 being disposed in right ventricle 200 of heart 115. Right atrium 205, left atrium 210, and left ventricle 215 are also illustrated. Distal end 140 of lead 110 includes at least one electrode, such as pacing tip electrode 220 and pacing ring electrode 225, for providing bipolar pacing stimulations to heart 115. Tip electrode 220 is coupled to device 105 by a first wire carried in lead 110. Ring electrode 225 is coupled to device 105 by a second wire carried in lead 110. Distal end 140 of lead 110 also includes a piezoelectric first ultrasonic element 230, located near ring electrode 225 and tip electrode 220, for transmitting ultrasound, receiving ultrasound, or both transmitting and receiving ultrasound. Device 105 includes a piezoelectric second ultrasonic element 235 for transmitting ultrasound, receiving ultrasound, or both transmitting and receiving ultrasound. In one embodiment, second ultrasonic element 235 is attached within a hermetically sealed case that encloses the electronic and other components of device 105. In another embodiment, second ultrasonic element 235 is included within a header portion extending from the hermetically sealed case, as illustrated in FIG. 6.

Figure 3:
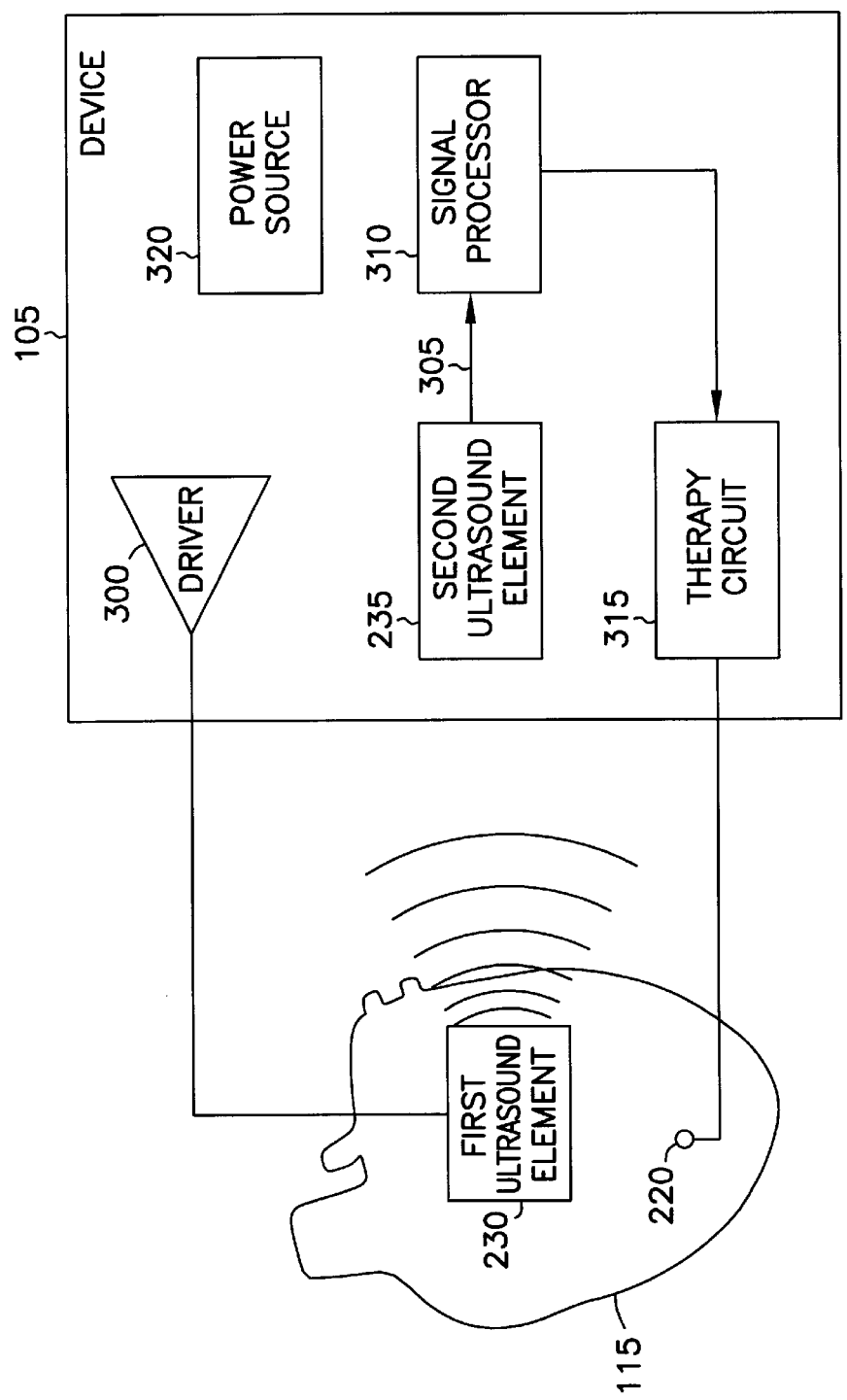
FIG. 3 is a schematic drawing illustrating generally one embodiment of portions of a lead, an implanted device, and circuits included in the implanted device.

FIG. 3 is a schematic drawing illustrating generally, by way of example, but not by way of limitation, portions of heart 115, including first ultrasound element 230 and at least one electrode 220 disposed therein, and device 105, including second ultrasound element 235. In this embodiment, an electrical driving signal at ultrasonic frequencies (e.g., 1–100 microsecond pulses of a 10 MHZ ultrasound signal) is provided by driver 300, in device 105, through conductors in lead 110 to first ultrasound element 230. Transduced from this signal, first ultrasound element 230 emits ultrasound energy within heart 115. This ultrasound energy is received by second ultrasound element 235 in device 105, which transduces it into an electrical signal that is provided, at node 305, to signal processor 310. Signal processor 310 includes amplification, demodulation, filter, analog-to-digital (A/D) conversion, digital-to-analog (D/A) conversion, memory, and other circuits for extracting and storing information obtained from the transduced ultrasound signal from second ultrasound element 235. Portions of these circuits may be implemented as one or more sequences of instructions carried out on a microprocessor or other microcontroller.

The signal at node 305 includes information about the movement of the heart chamber in which first ultrasound element 230 is disposed. Therapy circuit 315 delivers a pacing pulse stimulation via lead 110 to electrode 220 in right ventricle 200 (for example) of heart 115. Such pacing stimuli are usually delivered at a time when the particular heart chamber is in a relaxed passive state and is being filled with blood. If the delivered pacing stimulus captures the heart, myocardial tissue near pacing site of electrode 220 begins to contract. If the delivered pacing stimulus does not capture the heart, such tissue does not begin to contract.

In one embodiment, system 100 uses a measurement of the transit time of the ultrasound energy between first ultrasound element 230, which is disposed in right ventricle 200, and second ultrasound element 235, in device 105 located at a reference point elsewhere in patient 120 outside heart 115. The transit time of the ultrasound energy provides an indication of the physical distance between first ultrasound element 230 and second ultrasound element 235. Variations in this distance represent movement of right ventricle 200, in which first ultrasound element 230 is disposed, relative to device 105. Such movement of right ventricle 200 results from contractions caused by the pacing stimulations or intrinsic electrical heart activity. The presence or absence of such movement during an appropriate time period following the pacing stimulation indicates a resulting capture and no capture, respectively.

By monitoring movement over that portion of the cardiac cycle following the pacing stimulation, system 100 determines whether the pacing stimulation captured the heart. In one embodiment, the movement observed (during an appropriate time window initiated by the pacing stimulation) is compared to a threshold value, which corresponds to the movement expected even in the absence of an evoked contraction. If the movement observed exceeds this threshold value, then system 100 indicates that capture was successfully obtained. If, upon expiration of the appropriate time period, system 100 determines that the heart was not captured, then system 100 issues a second pacing stimulation, of sufficiently large energy to obtain capture. In another embodiment, movement is monitored over a plurality of cardiac cycles to determine whether, over a period of time, the pacing stimulations capture the heart. For each pacing stimulation, if no capture is indicated upon expiration of the time window triggered by the pacing stimulation, then a second pacing stimulation of sufficient energy to obtain capture is delivered.

One autocapture method of determining the appropriate energy level starts with the delivery of a high energy pacing stimulation to the heart. The energy is reduced during subsequent pacing stimulations (e.g., by reducing pacing amplitude or pulse duration), until the movement observed indicates that capture was not obtained. System 100 then increases the energy back to a level known to be adequate to obtain capture. This autocapture determination can be made intermittently or, alternatively, may represent a particular mode that can be set to operate continuously.

In another embodiment, system 100 uses a Doppler shift measurement of movement of the right ventricle 200. In this embodiment, the change in frequency of the ultrasound signals transmitted by the first ultrasound element 230 (and received by second ultrasound element 235) is frequency demodulated to represent movement of right ventricle 200 as it contracts and expands. A higher frequency signal represents motion of the first ultrasound element 230, in right ventricle 200, toward device 105. A lower frequency signal represents motion of the first ultrasound element 230, in right ventricle 200, away from device 105. In a further embodiment, both transit time and Doppler shift measurements (or other like measurements) are used.

System 100 includes an autocapture determination module (e.g., a sequence of instructions carried out on the microcontroller in signal processor 310) that determines whether motion of the heart chamber indicates a contraction in response to the delivered stimulation. The autocapture determination module adjusts the stimulation energy (either the amplitude of the pacing voltage pulse or the time period, i.e., pulsewidth, during which the pacing stimulation is being delivered) to provide only that stimulation energy which is needed to obtain capture. As a result, the energy delivered by therapy circuit 315 is optimized such that, over many such cardiac cycles, pacing stimulations are delivered at optimized reduced energies. This, in turn, prolongs the life of power source 320 (e.g., a battery) and the implanted device 105, minimizing the risk and expense to patient 120 associated with early explantation and replacement of device 105.

Figure 4:
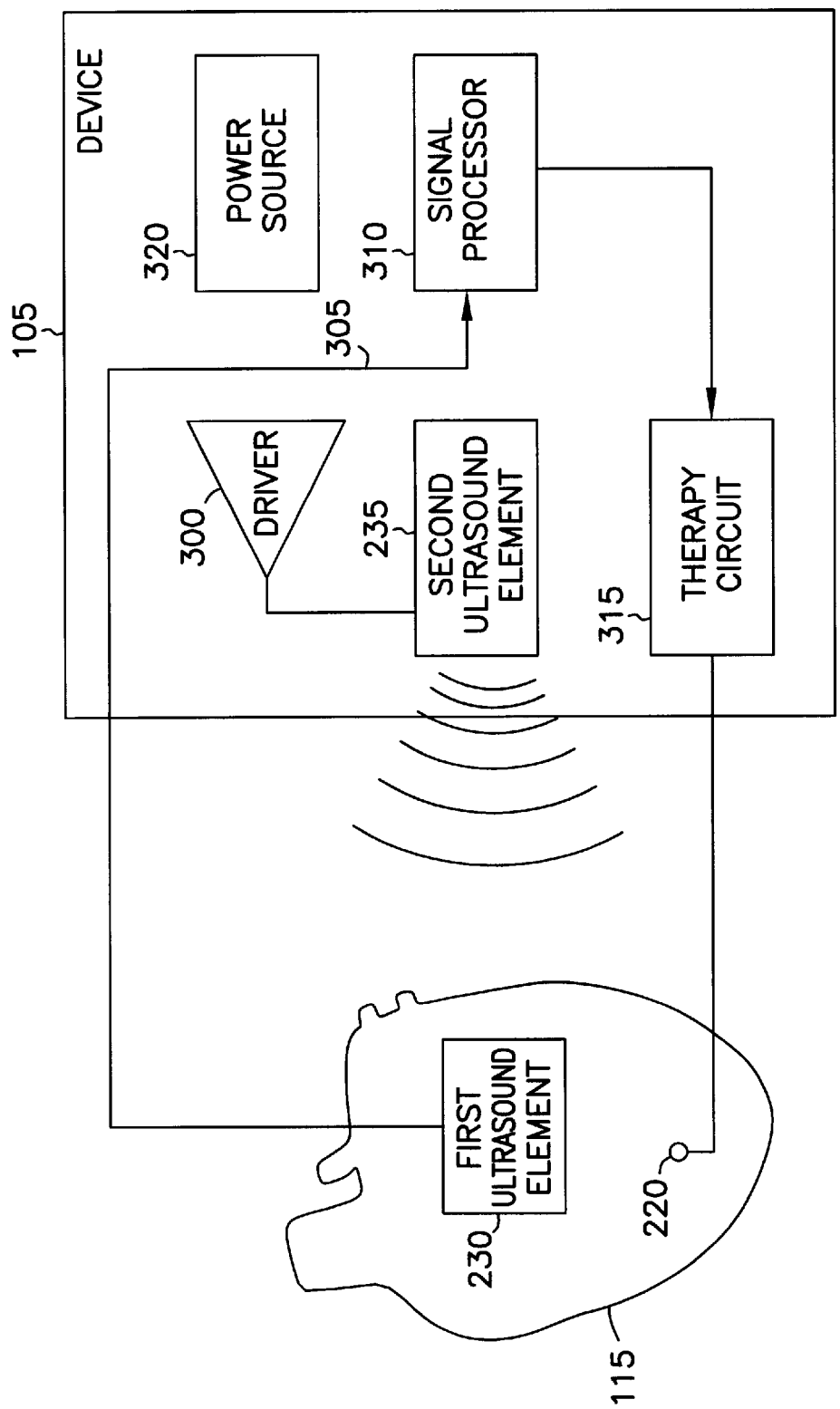
FIG. 4 is a schematic drawing, illustrating generally one embodiment of transmission of ultrasound from the device to the ultrasonic element disposed in the heart.

FIG. 4 is a schematic drawing, similar to FIG. 3, illustrating generally, by way of example, but not by way of limitation, another embodiment of portions of system 100 in which driver 300 is coupled to second ultrasound element 235 for emitting ultrasound energy received by first ultrasound element 230 in heart 115, where it is transduced into an electrical signal that is provided, at node 305, to signal processor 310. This embodiment also contemplates one or more of transit time, Doppler shift, or other like measurements of the motion of first ultrasound element 230 to detect whether a stimulation from therapy circuit 315 obtains a resulting contraction of heart 115.

Figure 5:
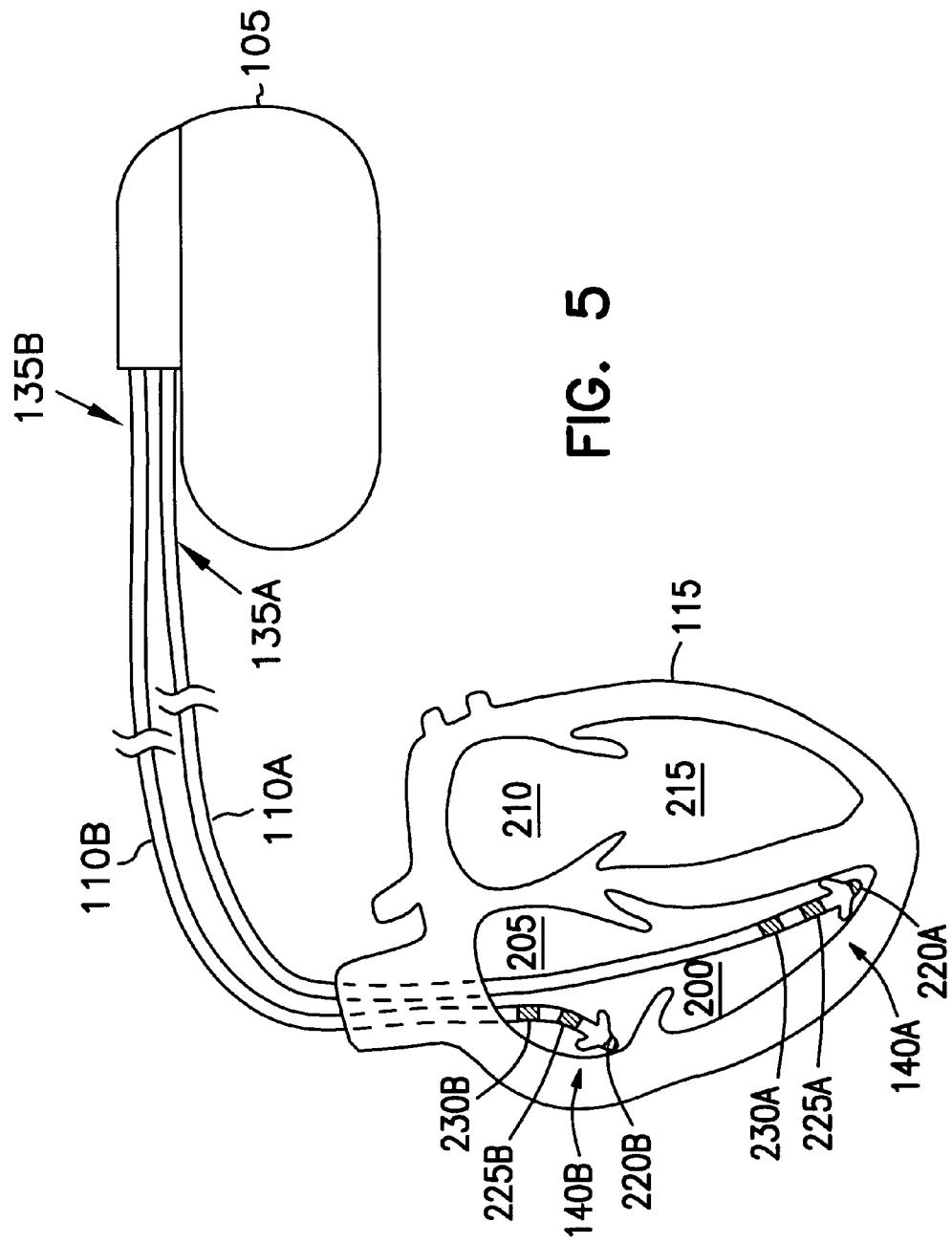
FIG. 5 is a schematic drawing, illustrating generally an embodiment including a first ultrasonic element in a first heart chamber and a second ultrasonic element disposed in another heart chamber.

FIG. 5 is a schematic drawing, including aspects that are similar to those described with respect to FIG. 2, illustrating generally, by way of example, but not by way of limitation, another embodiment of portions of system 100 in which device 105 is also coupled to a second heart chamber, i.e., right atrium 205, through lead 110B. Second lead 110B also includes tip electrode 220B, ring electrode 225B, and second ultrasonic element 230B. In this embodiment, a stimulation is delivered to right ventricle 200 and its movement is detected by providing ultrasound at first ultrasound element 230A and receiving the ultrasound at second ultrasound element 230B (or vice versa) to determine whether the stimulation obtained a resulting contraction of right ventricle 200. Similarly, a stimulation is delivered to right atrium 205 and its movement is detected by providing ultrasound at second ultrasound element 230B and receiving the ultrasound at first ultrasound element 230A (or vice versa) to determine whether the stimulation obtained a resulting contraction of right atrium 205.

FIG. 6 is a schematic drawing, similar to FIGS. 2 and 5, illustrating generally, by way of example, but not by way of limitation, another embodiment of portions of system 100 in which device 105 also includes a third ultrasonic element 235. This embodiment also illustrates, by way of example, locating third ultrasonic element 235 in a header portion extending from the hermetically sealed case. Alternatively, third ultrasonic element 235 is located in the hermetically sealed case, as illustrated in FIG. 2. In th embodiment of FIG. 6, a stimulation is delivered to right ventricle 200, and its movement is detected by providing ultrasound at first ultrasound element 230A and receiving the ultrasound at third ultrasound element 235 (or vice versa) to determine whether the stimulation obtained a resulting contraction of right ventricle 200. Similarly, a stimulation is delivered to right atrium 205, and its movement is detected by providing ultrasound at second ultrasound element 230B and receiving the ultrasound at third ultrasound element 235 (or vice versa) to determine whether the stimulation obtained a resulting contraction of right atrium 205.

Figure 7:
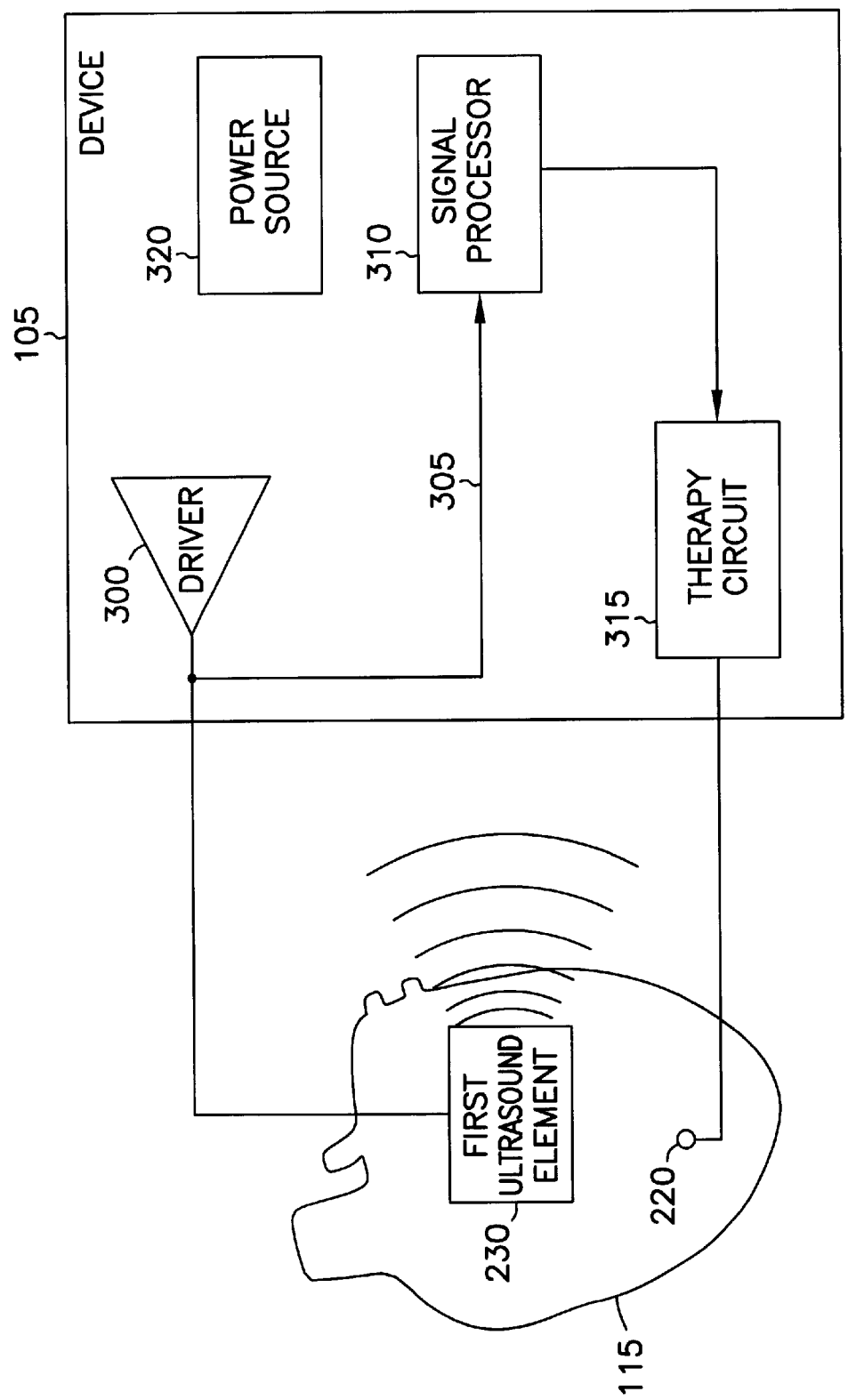
FIG. 7 is a schematic drawing illustrating generally an embodiment including a single ultrasonic element in a first heart chamber for both providing and receiving ultrasound energy.

FIG. 7 is a schematic drawing illustrating another embodiment of portions of system 100 in which a single ultrasound element, such as first ultrasound element 230, both provides and receives ultrasound energy. In this embodiment, first ultrasound element 230 is coupled to driver 300. Ultrasound element 230 converts electrical energy provided by driver 300 into an ultrasound energy pulse that is delivered to heart 115. Then, driver 300 is turned off, and ultrasound element 230 receives reflected ultrasound energy, such as from any acoustic boundary, for example, the interior wall of heart 115. The ultrasound energy reflected from the heart wall and received by ultrasound element 230 is transduced by ultrasound element 230 into an electrical signal that is provided, at node/bus 305 to signal processor 310.

In one embodiment, variations in the transit time of the received ultrasound energy that is reflected from the heart wall provides an indication of the movement of the heart due to a contraction. In another embodiment, variations in the Doppler shift of the received ultrasound energy that is reflected from the heart wall provides an indication of the movement of the heart due to a contraction. In a further embodiment, both transit time and Doppler shift measurements (or other like measurements) are used. Using the techniques described above, system 100 includes an ultrasound autocapture method that determines whether a particular pacing stimulation captured the heart based on the ultrasound indication of movement of the heart during a time window following the pacing stimulation.

OTHER APPLICATIONS

Figure 8:
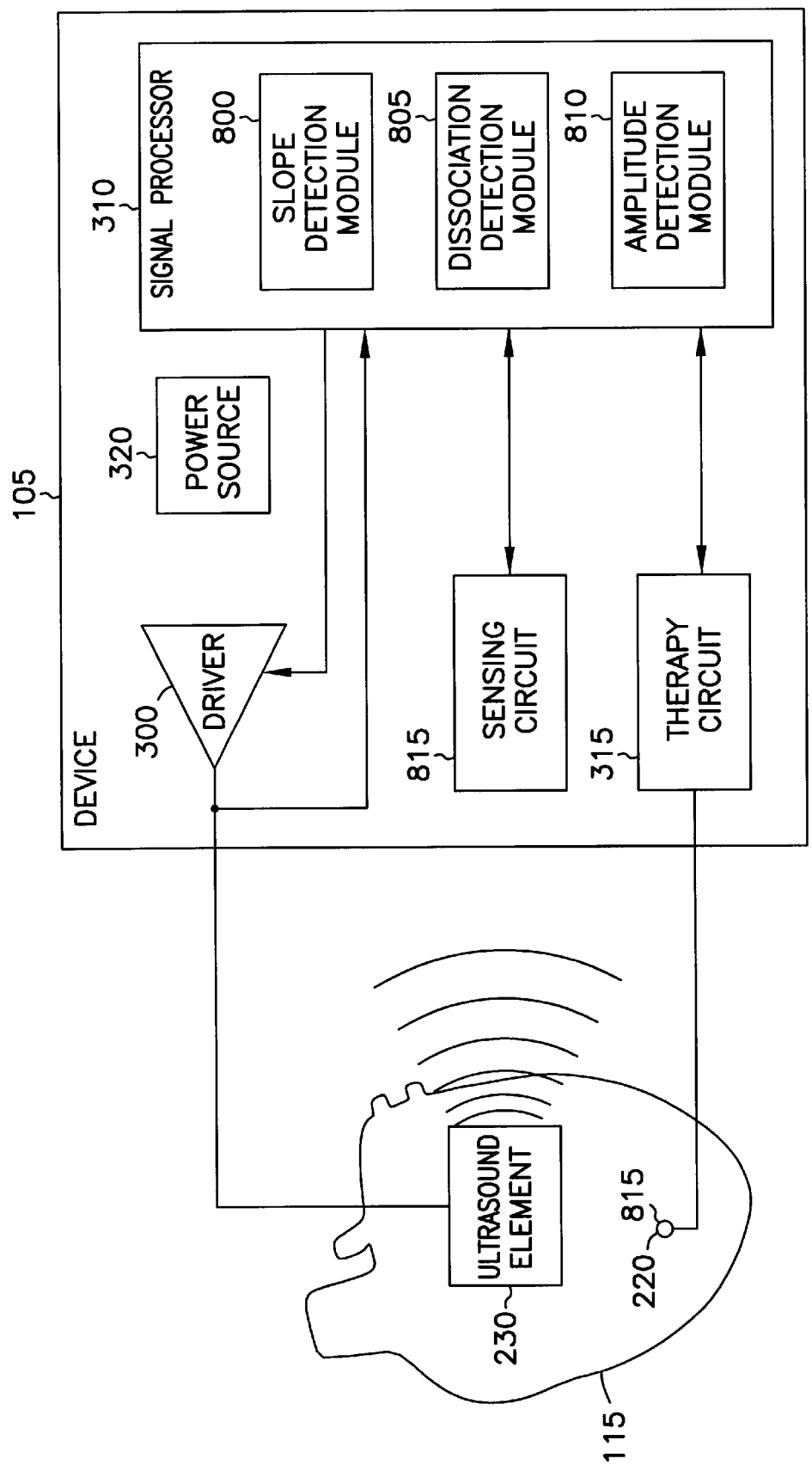
FIG. 8 is a schematic drawing illustrating generally an embodiment providing capabilities other than autocapture.

Although it is described above primarily with respect to using ultrasound for providing autocapture capability, system 100 includes also other uses, as illustrated generally, by way of example, but not by way of limitation, in the schematic drawing of FIG. 8. In a first example, the ultrasound signal provides information about mechanical heart contractions. The ultrasound signal is transduced and processed to obtain an electrical signal that includes information about the heart contractions. From the slope other characteristics of this electrical signal, a slope detection module 800 determines the strength of the heart contraction. In one embodiment, the slope detection module 800 is implemented as a sequence of instructions executed by signal processor 310. For example, stronger contractions occur during a shorter period of time, corresponding to a larger slope in the ultrasonically transduced mechanical heart contraction signal. This information is used for diagnostic purposes (e.g., communicated to programmer 125) or to adjust therapy, such as by adjusting rate, timing, or energy to maximize the strength of the heart contraction.

In a second example, the ultrasound signal provides information about mechanical heart contractions. Intrinsic electrical heart activity signals obtained, at sensing circuit 815, from the lead electrodes. These intrinsic electrical heart activity signals are also referred to as electrogram signals. The electrogram signals provide information about the electrical heart activity which causes the heart contractions. The ultrasound and the electrogram signals are compared by a dissociation detection module 805 implemented as a sequence of instructions executed in signal processor 310 to determine whether, and to what degree, there exists any dissociation between the time of intrinsic electrical heart activity and the corresponding resulting mechanical contractions of the heart. This information is used for diagnostic purposes (e.g., communicated to programmer 125) or to adjust therapy, such as by adjusting rate, timing, or energy delivered to optimize the relationship between intrinsic electrical heart activity and the mechanical contractions of the heart.

In a third example, the ultrasound signal provides information about mechanical heart contractions. The ultrasound signal is transduced and processed to obtain an electrical signal that includes information about the heart contractions. From the amplitude or other characteristics of this signal, the filling and end diastolic volume of the heart is determined. In one example, a amplitude detection module 810, such as a peak detection module implemented as a sequence of instructions executed in signal processor 310, is used to obtain an indirect measure of the volume of the heart using amplitude measurements. This information is used for diagnostic purposes (e.g., communicated to programmer 125). For example, increases in heart volume may indicate degeneration toward congestive heart failure (CHF). Alternatively, the ultrasonic signal information is used to adjust therapy, such as by adjusting rate, timing, or energy delivered to maximize cardiac output or efficiency.

In a fourth example, the ultrasound signal provides information about mechanical heart contractions. Electrogram signals, from sensing circuit 815, provide information about the electrical heart activity that causes the heart contractions. Such electrogram signals may include far-field sensing of electrical heart activity associated with heart chambers other than the heart chamber in which the electrode providing the signal is located. The ultrasonically obtained heart contraction information is used to augment the electrical heart activity information from sensing circuit 815 for better determining the origin of the sensed electrical heart activity (e.g., near-field or far-field) so that therapy can be provided based on a more accurate determination of heart activity. Conversely, the ultrasound signal may include components associated with heart chambers other than the heart chamber associated with the ultrasound element. In such a case, the electrogram information may alternatively be used to better determine the origin of the ultrasonically-indicated mechanical heart contraction signal so that therapy can be provided based on a more accurate determination of heart activity.

In a fifth example, the ultrasound signal provides information about mechanical heart contractions. Electrogram signals from sensing circuit 815 provide information about the electrical heart activity that causes the heart contractions. Certain arrhythmias, such as sinus tachycardia and ventricular tachycardia are difficult to distinguish from each other based on electrogram signals. Moreover, defibrillation countershock therapy may be appropriate for a ventricular tachycardia, but unnecessary for a sinus tachycardia. However, the mechanical heart contraction signal characteristics are different for sinus tachycardia as compared to ventricular tachycardia. In one embodiment, system 100 discriminates between sinus tachycardia, ventricular tachycardia, and other arrhythmias based on the mechanical heart contraction signal obtained from one or more ultrasound elements disposed in one or more of right ventricle 200, right atrium 205, or other heart chamber. Antitachyarrhythmia therapy is tailored to the particular type of arrhythmia detected. In one embodiment, defibrillation countershocks are delivered for ventricular tachyarrhythmias, but are not delivered for sinus tachyarrhythmias. System 100 saves energy by avoiding the inappropriate delivery of defibrillation countershocks for sinus tachyarrhythmias. This minimizes the risk and expense to patient 120 associated with early explantation and replacement of device 105. Avoiding inappropriate delivery of defibrillation countershocks also avoids irritating the heart and causing further arrhythmias. Even more importantly, system 100 decreases the risk of actually causing a ventricular tachyarrhythmia, such as life-threatening ventricular fibrillation, by inappropriately delivering a shock.

In a sixth example, the signal processor 310 controls operation of endocardial ultrasonic element 225 such that it delivers localized ultrasound energy pulses to at least partially disrupt cell membranes near the pacing tip electrode 220. This is expected to lower the pacing threshold energy required to capture the heart 115 by decreasing the electrical resistance of cell membranes near the pacing electrode. One or more pacing pulses are then delivered at reduced energies, such as by using the autocapture techniques described above. This prolongs the usable life of implanted device 105. In one embodiment, delivery of the ultrasound energy pulse is synchronized to delivery of a pacing pulse.

In a seventh example, the signal processor 310 controls operation of endocardial ultrasonic element 225 such that it modulates the release of a steroid from a nearby steroid eluting element, such as a polymeric steroid eluting matrix.

In one example, a steroid eluting matrix is associated with nearby pacing electrode 220 to reduce the formation of scar tissue after implant so that lower pacing threshold energies are obtained. In one embodiment, device 105 delivers ultrasound energy to enhance the rate of steroid delivery. Because device 105 can accurately control the timing, duration, and energy of the ultrasound, increased control is obtained over the release of the steroid, which is ordinarily governed primarily by the physical characteristics of the steroid eluting matrix. In one embodiment, device 105 is programmably operated to release the steroid either more immediately after implant or after a desired time delay.

In an eighth example, the endocardial ultrasonic element 225 is used to measure blood flow in the heart chamber in which it is disposed, using transit time, Doppler shift, or other measurement techniques. This blood flow information is used for diagnostic purposes or to adjust therapy, such as by adjusting rate, timing, or energy delivered to maximize cardiac output based on the blood flow measurements.

CONCLUSION

The above-described system provides, among other things, a cardiac rhythm management system with ultrasound autocapture capability for determining whether a stimulation has evoked a desired response from the heart, and for adjusting an energy of the stimulation based on the observed response from the heart. An autocapture determination circuit determines whether motion of the heart chamber indicates a contraction in response to the stimulation, and adjusts the stimulation energy to provide only that energy which is needed to obtain capture. This saves energy, prolonging the life of the implanted device, minimizing the risk and expense to a patient associated with early explantation and replacement of the implanted device.

Although the system was described above primarily with respect to disposing an ultrasound element in the right ventricle for autocapture determination, it is understood that the system also includes application to ultrasonic autocapture determination in other heart chambers, and to the use of ultrasound for applications other than autocapture, some of which are described above.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm management system comprising:
   a lead, comprising a distal end and a proximal end, the distal end of the lead adapted for being disposed in or about a heart, the distal end of the lead comprising a first ultrasonic element; and
   an electronics unit coupled to the proximal end of the lead, the electronics unit comprising:
      an ultrasound driving circuit; and
      a signal processing circuit that processes a signal that is based on ultrasound, and in which the signal processing circuit includes an autocapture determination module that determines, using information from the signal that is based on ultrasound, whether a stimulus triggered a resulting heart contraction.

2. The system of claim 1, further comprising:
   an electrode adapted for being associated with a portion of a heart; and
   a sensing circuit for detecting intrinsic electrical heart activity based on at least one electrogram signal received from the electrode.

3. The system of claim 2, in which the signal processing circuit detects occurrences of heart activity using both the ultrasound and the electrogram signal.

4. The system of claim 1, further comprising a programmer remote from the electronics unit.

5. A cardiac rhythm management system comprising:
   an electronics unit, sized and shaped to permit implantation in a human subject, the electronics unit comprising:
      an ultrasound driving circuit; and
      means for determining, using information from returned ultrasound, whether an electrical stimulus triggered a resulting heart contraction.

6. The system of claim 5, further comprising a lead coupled to the electronics unit, the lead comprising a distal end and a proximal end, the distal end of the lead adapted for being disposed in or about a heart, the distal end of the lead comprising a first ultrasonic element.

7. The system of claim 5, further comprising a lead coupled to the electronics unit, the lead comprising a distal end and a proximal end, the distal end of the lead adapted for being disposed in or about a heart, the distal end of the lead comprising an electrode for delivering the electrical stimulus.

8. A cardiac rhythm management system comprising:
   an electronics unit, sized and shaped to permit implantation into a human subject, the electronics unit comprising:
      an ultrasound driving circuit; and
      a signal processing circuit that processes a signal that is based on ultrasound, and in which the signal processing circuit includes a slope detection module that provides, using information from the signal that is based on ultrasound, an indication of a strength of a mechanical heart contraction.

9. The system of claim 8, further comprising a lead, coupled to the electronics unit, the lead comprising a distal end and a proximal end, the distal end of the lead adapted for being disposed in or about a heart, the distal end of the lead comprising a first ultrasonic element.

10. A cardiac rhythm management system comprising:
    an electronics unit, sized and shaped to permit implantation into a human subject, the electronics unit comprising:
       an ultrasound driving circuit; and
       means for determining a strength of a mechanical heart contraction using information from a signal that is based on ultrasound.

11. A cardiac rhythm management system comprising:
    an electronics unit coupled to the proximal end of the lead, the electronics unit sized and shaped to permit implantation into a human subject, the electronics unit comprising:
       an ultrasound driving circuit; and
       a signal processing circuit that processes a signal that is based on ultrasound, and in which the signal processing circuit includes an amplitude detection module that detects an amplitude of the signal that is based on ultrasound.

12. The system of claim 11, in which the amplitude detection module provides an indication of the volume of a mechanical heart contraction using the detected amplitude of the signal that is based on ultrasound.

13. The system of claim 11, further comprising a lead, comprising a distal end and a proximal end, the distal end of the lead adapted for being disposed in or about a heart, the distal end of the lead comprising a first ultrasonic element.

14. A cardiac rhythm management system comprising:
an electronics unit, sized and shaped to permit implantation into a human subject, the electronics unit configured to be coupled to an electrode associated with a heart and to an ultrasonic element associated with the heart, the electronics unit comprising:
an ultrasound driving circuit;
a signal processing circuit that processes a signal that is based on returned ultrasound;
a sensing circuit to detect intrinsic electrical heart activity using at least one electrogram signal received from the electrode, and
in which the signal processing circuit is configured to detect a dissociation between (1) an occurrence of heart activity detected using the signal that is based on returned ultrasound and (2) an occurrence of heart activity detected using the at least one electrogram signal.

15. The system of claim 14, further comprising a lead comprising a distal end and a proximal end, the distal end of the lead adapted for being disposed in or about a heart, the distal end of the lead comprising the ultrasonic element associated with the heart.

16. The system of claim 14, further comprising a lead comprising a distal end and a proximal end, the distal end of the lead adapted for being disposed in or about a heart, the distal end of the lead comprising the electrode associated with the heart.

17. The system of claim 14, further comprising a lead comprising a distal end and a proximal end, the distal end of the lead adapted for being disposed in or about a heart, the distal end of the lead comprising the electrode associated with the heart and the ultrasonic element associated with the heart.

18. A cardiac rhythm management system comprising:
an electronics unit, sized and shaped to permit implantation into a human subject, the electronics unit configured to be coupled to an electrode associated with a heart and to an ultrasonic element associated with the heart, the electronics unit comprising:
an ultrasound driving circuit;
a sensing circuit to detect intrinsic electrical heart activity using at least one electrogram signal received from the electrode; and
means, coupled to the sensing circuit, for detecting any dissociation between (1) an occurrence of heart activity detected using returned ultrasound and (2) an occurrence of heart activity detected using the at least one electrogram signal.

19. The system of claim 18, further comprising a lead comprising a distal end and a proximal end, the distal end of the lead adapted for being disposed in or about a heart, the distal end of the lead comprising the ultrasonic element associated with the heart.

20. The system of claim 18, further comprising a lead comprising a distal end and a proximal end, the distal end of the lead adapted for being disposed in or about a heart, the distal end of the lead comprising the electrode associated with the heart.

21. The system of claim 18, further comprising a lead comprising a distal end and a proximal end, the distal end of the lead adapted for being disposed in or about a heart, the distal end of the lead comprising the electrode associated with the heart and the ultrasonic element associated with the heart.

* * * * *